(12) United States Patent
Junker et al.

(10) Patent No.: US 7,585,648 B2
(45) Date of Patent: Sep. 8, 2009

(54) NUCLEIC ACIDS ENCODING NEUTRALIZING GDF8 EPITOPE-BASED PEPTIDES AND FUSION PROTEINS

(75) Inventors: David E. Junker, San Diego, CA (US); Mark D. Cochran, Carlsbad, CA (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 0 days.

(21) Appl. No.: 12/061,012

(22) Filed: Apr. 2, 2008

(65) Prior Publication Data

US 2008/0227156 A1    Sep. 18, 2008

Related U.S. Application Data

(62) Division of application No. 11/019,001, filed on Dec. 21, 2004, now Pat. No. 7,371,726.

(60) Provisional application No. 60/533,719, filed on Dec. 31, 2003.

(51) Int. Cl.
```
C12N 15/11    (2006.01)
C12N 15/62    (2006.01)
C12N 15/63    (2006.01)
C12N 15/64    (2006.01)
C12N 1/21     (2006.01)
C12N 5/10     (2006.01)
```
(52) U.S. Cl. .................. 435/69.7; 435/69.1; 435/320.1; 435/325; 435/252.3; 536/23.1; 536/23.4; 530/300

(58) Field of Classification Search .................. None
See application file for complete search history.

(56) References Cited

U.S. PATENT DOCUMENTS

| | | | |
|---|---|---|---|
| 5,422,110 A | 6/1995 | Potter et al. | |
| 5,476,657 A | 12/1995 | Potter et al. | |
| 5,708,155 A | 1/1998 | Potter et al. | |
| 5,827,733 A | 10/1998 | Lee et al. | |
| 5,871,750 A | 2/1999 | Potter | |
| 5,977,438 A | 11/1999 | Turpen et al. | |
| 6,004,937 A | 12/1999 | Wood et al. | |
| 6,042,832 A | 3/2000 | Koprowski et al. | |
| 6,096,506 A | 8/2000 | Lee et al. | |
| 6,368,597 B1 | 4/2002 | Strassman et al. | |
| 6,369,201 B1 | 4/2002 | Barker et al. | |
| 6,399,312 B2 | 6/2002 | Wu-Wong et al. | |
| 6,468,535 B1 | 10/2002 | Lee et al. | |
| 6,607,884 B1 | 8/2003 | Lee et al. | |
| 6,617,440 B1 | 9/2003 | Findly | |
| 6,656,475 B1 | 12/2003 | Lee et al. | |
| 6,730,306 B1 | 5/2004 | Pogue et al. | |
| 7,037,501 B2 * | 5/2006 | El Halawani et al. | 424/185.1 |
| 7,056,512 B1 * | 6/2006 | Klysner et al. | 424/185.1 |
| 7,070,784 B1 * | 7/2006 | Halkier et al. | 424/185.1 |
| 2001/0014330 A1 | 8/2001 | Harland et al. | |
| 2002/0127234 A1 | 9/2002 | El Halawani et al. | |
| 2002/0157125 A1 | 10/2002 | Lee et al. | |
| 2003/0065137 A1 | 4/2003 | Barker et al. | |
| 2003/0074680 A1 | 4/2003 | Lee et al. | |
| 2006/0159696 A1 | 7/2006 | Junker et al. | |
| 2006/0281075 A1 | 12/2006 | Smith et al. | |

FOREIGN PATENT DOCUMENTS

| | | |
|---|---|---|
| EP | 0 690 873 B1 | 6/2003 |
| GB | 2 333 706 A | 8/1999 |
| WO | WO 98/33887 A1 | 8/1998 |
| WO | WO 99/42573 A1 | 8/1999 |
| WO | WO 01/26672 A1 | 4/2001 |
| WO | WO 03/027248 A2 | 4/2003 |
| WO | WO 2004/052930 A2 | 6/2004 |
| WO | WO 2004/058988 A2 | 7/2004 |

OTHER PUBLICATIONS

Geysen et al., "Use of peptide synthesis to probe viral antigens for epitopes to a resolution of single amino acid", Proc. Natl. Acad. Sci. USA, 81(1):3998-4002 (Jul. 1984).
Gonzalez-Cadavid et al., "Organization of the human myostatin gene and expression in healthy men and HIV-infected men with muscle wasting," Proc. Natl. Acad. Sci. USA, 95:14938-14943 (Dec. 1998).
McPherron et al., "Regulation of skeletal muscle mass in mice by a new TGF-β superfamily member", Nature, 387:83-90 (May 1997).
PCT International Search Report dated May 25, 2005 for corresponding PCT Application No. PCT/US2004/043125.
PCT International Search Report mail date Sep. 20, 2006 for corresponding PCT application No. PCT/US2005/046363, international filing date Dec. 21, 2005.
R&D Systems, Inc., Antibody Reference Guide and Catalog, May 1, 2003.
Rebbapragada et al., "Myostatin signals through a transforming growth factor β-like signaling pathway to block adipogenesis", Molecular and Cellular Biology, 23(20):7230-7242 (Oct. 2003).

* cited by examiner

Primary Examiner—Elizabeth C. Kemmerer

(57) ABSTRACT

The invention provides new, specific nucleic acids encoding antigenic peptides from the protein GDF8. The invention also provides nucleic acids encoding fusion proteins comprising the new peptides, immunogens and vaccines based on the nucleic acids encoding new peptides and/or fusion proteins, antibodies that specifically bind to the new peptides of GDF8, and methods of treating animals in order to modulate the activity of GDF8, employing vaccines or antibodies according to the invention.

25 Claims, 2 Drawing Sheets

FIG. 2

GDF8 Peptides Corresponding to DJ5
Residue Nos. Based on Precursor GDF8: 327 → 346

Animal Species and Genebank Nos. For the complete precursor GDF8 of Each Cited Species

| 327 | | | | | | | | | | | | | | | | | | | 346 | Species |
|---|---|---|---|---|---|---|---|---|---|---|---|---|---|---|---|---|---|---|---|---|
| V | H | Q | A | N | P | R | G | S | A | G | P | C | C | T | P | T | K | M | S | Anas platyrhynchos (duck) AAL35275 |
| V | H | Q | A | N | P | R | G | S | A | G | P | C | C | T | P | T | K | M | S | Anser anser (goose) AAL35276 |
| V | H | Q | A | N | P | R | G | S | A | G | P | C | C | T | P | T | K | M | S | Anser anser (goose) AAR18246 |
| V | H | Q | A | N | P | R | G | S | A | G | P | C | C | T | P | T | K | M | S | Bos taurus (cow) AAB86687 |
| V | H | Q | A | N | P | R | G | S | A | G | P | C | C | T | P | T | K | M | S | Canis familiaris (dog) AAR14343 |
| V | [L] | Q | A | N | P | R | G | S | A | G | P | C | C | T | P | T | K | M | S | Capra hircus (goat) AAR12161 |
| V | H | Q | A | N | P | R | G | S | A | G | P | C | C | T | P | T | K | M | S | Columba livia (pigeon) AAL35277 |
| V | H | Q | A | N | P | R | G | S | A | G | P | C | C | T | P | T | K | M | S | Coturnix chinensis (quail) AAL35278 |
| V | H | [N] | A | [S] | N | [K] | G | [T] | A | G | P | C | C | T | P | T | K | M | S | Danio rerio (zebrafish) AAB86693 |
| V | H | Q | A | N | P | R | G | S | A | G | P | C | C | T | P | T | K | M | S | Equus caballus (horse) BAB16046 |
| V | H | Q | A | N | P | R | G | S | A | G | P | C | C | T | P | T | K | M | S | Gallus gallus (chicken) AAK18000 |
| V | H | Q | A | N | P | [K] | G | [P] | A | G | P | C | C | T | P | T | K | M | S | Gallus gallus (chicken) AAR18244 |
| V | H | Q | A | N | P | R | G | S | A | G | P | C | C | T | P | T | K | M | S | Homo sapiens (human) NP_005250 |
| V | H | [N] | A | [S] | N | [K] | G | [T] | A | G | P | C | C | T | P | T | K | M | S | I. punctatus (catfish) AAK84666 |
| V | H | Q | A | N | P | R | G | S | A | G | P | C | C | T | P | T | K | M | S | Lepus capensis (hare) AAN87890 |
| V | H | Q | A | N | P | R | G | S | A | G | P | C | C | T | P | T | K | M | S | Macaca fascicularis (monkey) AAL17640 |
| V | H | Q | A | N | P | R | G | S | A | G | P | C | C | T | P | T | K | M | S | Meleagris gallopavo (turkey) AAB86692 |
| V | H | [N] | A | [S] | N | [K] | G | [T] | A | G | P | C | C | T | P | T | K | M | S | Morone chrysops (white bass) AAK28707 |
| V | H | Q | A | N | P | R | G | S | A | G | P | C | C | T | P | T | K | M | S | Mus musculus (house mouse) AAC53167 |
| V | H | [N] | A | [S] | N | [K] | G | [T] | A | G | P | C | C | T | P | T | K | M | S | O. mykiss (trout) AAK71707 |
| V | H | Q | A | N | P | R | G | S | A | G | P | C | C | T | P | T | K | M | S | Ovis aries (sheep) AAB86689 |
| V | H | Q | A | N | P | R | G | S | A | G | P | C | C | T | P | T | K | M | S | Papio hamadryas (baboon) AAB86686 |
| V | H | Q | A | N | P | R | G | S | A | G | P | C | C | T | P | T | K | M | S | Rattus norvegicus (rat) AAB86691 |
| V | H | [N] | A | [S] | N | [K] | G | [T] | A | G | P | C | C | T | P | T | K | M | S | Salmo salar (salmon) CAC19541 |
| V | H | [N] | A | [S] | N | [K] | G | [T] | A | G | P | C | C | T | P | T | K | M | S | Sparus aurata (seabream) AAL05943 |
| V | H | Q | A | N | P | R | G | S | A | G | P | C | C | T | P | T | K | M | S | Sus scrofa (pig) AAC08035 |
| V | [L] | [Q] | A | N | P | R | G | S | A | G | P | C | C | T | P | T | K | M | S | Sus scrofa (pig) AAR18245 |

US 7,585,648 B2

NUCLEIC ACIDS ENCODING NEUTRALIZING GDF8 EPITOPE-BASED PEPTIDES AND FUSION PROTEINS

CROSS-REFERENCE TO RELATED APPLICATIONS

This application is a divisional application of U.S. Ser. No. 11/019,001 filed Dec. 21, 2004, now U.S. Pat. No. 7,371,726 B2, which is a non-provisional application that claims priority under 35 U.S.C. § 119(e) of provisional application U.S. Ser. No. 60/533,719 filed Dec. 31, 2003, the contents of both of which are hereby incorporated by reference in their entireties.

FIELD OF THE INVENTION

The invention relates to the protein growth differentiation factor 8, and to antigenic peptide fragments of growth differentiation factor 87 and related immunogens, vaccines, and methods of treating animals in order to modulate the activity of growth differentiation factor 8.

BACKGROUND OF THE INVENTION

Growth differentiation factor 8 is a protein that is classified with the transforming growth factor-β ("TGF-β") superfamily. Generally, the proteins of the TGF-β superfamily are initially expressed as precursor (a/k/a prohormone) that undergoes proteolytic cleavage at a cluster of basic residues about 110-140 amino acids from the precursor protein C-terminus. In each case, the active, or mature, TGF-β species is believed to be a disulfide-linked dimer of the cleaved precursor protein C-terminal regions.

Growth differentiation factor 8, hereinafter GDF8, is also art-known as GDF-8 or myostatin. The genes encoding the precursor of GDF8 (hereinafter "precursor GDF8") have been cloned from a wide range of organisms. These include the human and murine precursor GDF8[Nestor et al., 1998, Proc. Natl. Acad. Sci. 95:14938-43; U.S. Pat. No. 5,827,733, the contents of which are hereby incorporated by reference in their entireties]. It has also been reported that GDF8 immunoreactivity is detectable in human skeletal muscle in both type 1 and type 2 fibers. Antibodies and assays for detecting GDF8 are described, e.g., by U.S. Pat. No. 6,096,506.

It has further been reported that GDF8 plays a role in down-regulating or inhibiting the growth and development of skeletal muscle, as conformed by GDF8 knock-out mice (McPherron et al., 1997, Nature 3387-90). For this reason, there have been previous attempts, particularly in the field of animal husbandry, to modulate GDF8 activity in animals by several means, with the goal of down-regulating GDF8 activity in order to enhance the growth, and/or relative muscle mass, of various food animals.

For examples U.S. Pat. No. 6,399,312 describes a precursor GDF8 gene promoter and an assay, with the proposal that the assay be used to identify a theoretical inhibitor of that promoter. U.S. Pat. No. 6,656,475 describes a method of inhibiting the effect of GDF8 on a cell by contacting the cell with a GDF8 prodomain that competes for a GDF8 receptor, and reports that the C-terminus of mature GDF8 may vary. U.S. Pat. No. 6,004,937 describes the use of follistatin as a possible antagonist of GDF8. None of these methods has resulted in any practical applications in the fields of animal husbandry or clinical applications (either human or veterinary).

Others have also attempted to employ antibody and vaccine technology for downregulating GDF8 function. For instance, U.S. Pat. No. 6,369,201 [the contents of which are hereby incorporated by reference in their entireties], describes peptides, i.e., fragments of GDF8 protein, and a vaccine for eliciting anti-GDF8 antibodies. That patent also reported an unspecified degree of growth or weight gain, relative to controls, in rodents immunized with several of the reported GDF8 peptide fragments.

Other physiological roles for GDF8 have also been described. For example, U.S. Pat. No. 6,368,597, [the contents of which are hereby incorporated by reference in their entireties] has suggested that inhibiting GDF8 function is useful for treating Type II diabetes, e.g. by administering an anti-GDF8 antibody or anti-GDF8 vaccine to a patient having this condition.

Nevertheless, there remains a longstanding need in the art for improved antigens and immunogens for eliciting an anti-GDF8 immune response, as well as for improved GDF8 antibodies capable of highly specific binding to GDF8.

The citation of any reference herein should not be construed as an admission that such reference is available as "Prior Art" to the instant application.

SUMMARY OF THE INVENTION

The present invention solves these and other shortcomings in the art by providing GDF8 peptides (e.g., peptide fragments of GDF8 of 50 residues or less) comprising a specific neutralizing epitope for GDF8.

In one embodiment of the invention, GDF8 peptides are provided that include, for example, an isolated peptide that comprises from about residue 312 to about residue 361 of natural, human precursor GDF8 (SEQ ID NO:1). Preferably, the inventive GDF8 peptide comprises from about residue 320 to about residue 350, more preferably comprises from about residue 321 to about residue 346 and most preferably comprises from about residue 327 to about residue 346 of natural, human precursor GDF8. The exemplified GDF8 peptide, labeled as DJ5 hereinbelow, is illustrated as follows, in both single and triple letter code, along with residue numbering based on the precursor GDF8 of SEQ ID NO:1, for convenience.

```
DJ5
                                              (SEQ ID NO:8)
 327 328 329 330 331 332 333 334 335 336 337 338
  V   H   Q   A   N   P   R   G   S   A   G   P
 Val His Gln Ala Asn Pro Arg Gly Ser Ala Gly Pro 339 340 341 342 343 344 345 346
  C   C   T   P   T   K   M   S
 Cys Cys Thr Pro Thr Lys Met Ser
```

In a further embodiment of the invention, the GDF8 peptide optionally includes conservative single amino acid substitutions. Simply by way of example, these can be from one through at least five amino acid positions within the peptide. In a particular embodiment, there is at least one conservative amino acid substitution, e.g., between residues 327 to 346 of GDF8. In another embodiment, the GDF8 peptide includes conservative amino acid substitutions at no more than five amino acid positions within the peptide. In still another embodiment there are two conservative amino acid substitutions between residues 327 to 346 of GDF8. In yet another embodiment, there are three conservative amino acid substitutions between residues 327 to 346 of GDF8. In still another embodiment, there are four conservative amino acid substitutions between residues 327 to 346 of GDF8.

Preferably, the amino acid residue substitutions are at one or more positions, relative to natural, human precursor GDF8 (SEQ ID NO: 1) that are marked by the amino acid variations of the interspecies alignment of FIG. 2. These are at residues 328, 329, 331, 333 and 335, and combinations thereof, wherein, (a) amino acid residue 328 is His, Leu or Asn;
(b) amino acid residue 329 is Gln or Lys;
(c) amino acid residue 331 is Asn or Ser;
(d) amino acid residue 333 is Arg or Lys; and/or
(e) amino acid residue 335 is Ser, Pro or Thr.

Preferably, such modified GDF8 peptides comprise a specific neutralization epitope for an anti-GDF8 antibody and therefore retain the property of specifically binding to an anti-GDF8 antibody, where the antibody is mAb 788 and/or an IgG fraction of goat anti-GDF8 polyclonal antiserum, as exemplified hereinbelow.

In still a further embodiment of the invention, nucleic acid molecules, i.e., polynucleotides, encoding the above-mentioned GDF8 peptides are provided.

Preferably, the nucleic acid molecules include a section of the naturally occurring human precursor GDF8 gene, from about nucleotide 1112 to about nucleotide 1171 of the (Genebank accession NM_005259, human GDF8 gene; SEQ ID NO: 2). This section encodes peptide DJ5, as described above. Note that the NM_005259 record includes a large amount of sequence flanking the actual coding region. The artisan will also appreciate that the DJ5 corresponds to nucleotides 979-1038 of the actual coding region of the GDF8 prohormone.

Replicable cloning vectors, and prokaryotic or eukaryotic host cells comprising the nucleic acid molecules are also provided, along with methods of producing a GDF8 peptide that include the steps of: culturing the host cell(s), expressing the encoded peptide, and recovering the peptide. The artisan will also appreciate that the inventive GDF8 peptide will also be readily produced by any standard, art-known chemical synthetic method.

In yet a further embodiment of the invention, a vaccine composition that comprises the inventive GDF8 peptide (or fusion protein thereof) is also provided, e.g., that preferably includes one or more adjuvants and other art-standard elements of a peptide or protein-based vaccine composition. Methods of eliciting an anti-GDF8 immune response in an animal, comprising administering to the animal an effective amount of the vaccine composition, are also provided.

In another further embodiment, a screening method is provided for selecting an anti-GDF8 antibody or antibody fragment from among a plurality of antibodies or antibody fragments, comprising contacting the peptide with one or a plurality of antibodies or antibody fragments, and detecting antibody or antibody fragment that selectively binds to the peptide.

In yet another aspect, the present invention provides a method of down-regulating GDF8 activity in an animal. In one such embodiment, the method comprises administering an antibody or antibody fragment to the animal, in an amount and for a duration effective to down-regulate GDF8 activity in the animal, wherein the antibody binds specifically to the peptide, or by immunizing the animal with a vaccine composition as described herein. The animal is preferably a vertebrate, and more preferably a mammal, avian or fish. Preferably, the mammal is a domesticated animal (e.g., one used in animal husbandry, or alternatively, a companion animal) but can optionally be a human in need of such GDF8 downregulation.

The invention also contemplates fusion proteins incorporating the inventive GDF8 peptides. The fusion proteins can include domains that are signal peptides, for enhanced secretion or cell surface expression of the GDF8 fusion protein and/or to permit purification with a selective binding system. Further, the fusion proteins are contemplated to link one or more GDF8 peptides in a single carrier protein in order to enhance immunogenicity of the GDF8 peptide domain. In a particular embodiment, a fusion protein of the present invention comprises a GDF8 peptide consisting of 50 or fewer amino acid residues that comprises amino acid residues 327 to 346 of SEQ ID NO:1. In a related embodiment of this type, the fusion protein comprises an antigenic subfragment of that GDF8 peptide, e.g., a GDF8 peptide comprising about 10 consecutive amino acid residues from DJ5 (SEQ ID NO:8).

BRIEF DESCRIPTION OF THE DRAWINGS

FIG. 2 illustrates the alignment of the human DJ5 peptide sequence (SEQ ID NO: 8) compared to the analogous 20-residue peptides, as located in the precursor GDF8 proteins of the recited additional animal species. The amino acid residue positions of 321 through 347 are based on the human precursor GDF8. The Genebank accession numbers (incorporated by reference herein) identify the entire published protein sequence for that species.

Figure 1:
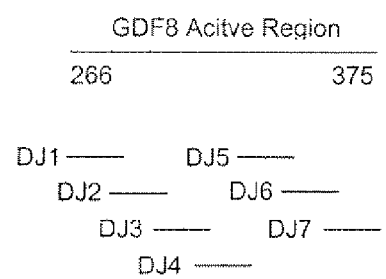
FIG. 1 illustrates overlapping peptides DJ1 through DJ7, in the GDF8 active region (i.e., mature GDF8), that is from residues 266-375 of the precursor GDF8 sequence.

The aligned peptides have the following SEQ ID NOs.

| | |
|---|---|
| *Anas platyrhynchos* (duck) AAL35275 | (SEQ ID NO: 11) |
| *Anser anser* (goose) AAL35276 | (SEQ ID NO: 12) |
| *Anser anser* (goose) AAR18246 | (SEQ ID NO: 13) |
| *Bos taurus* (cow) AAB86687 | (SEQ ID NO: 14) |
| *Canis familiaris* (dog) AAR14343 | (SEQ ID NO: 15) |
| *Capra hircus* (goat) AAR12161 | (SEQ ID NO: 16) |
| *Columba livia* (pigeon)AAL35277 | (SEQ ID NO: 17) |
| *Coturnix chinensis* (quail) AAL35278 | (SEQ ID NO: 18) |
| *Danio rerio* (zebrafish)AAB86693 | (SEQ ID NO: 19) |
| *Equus caballus* (horse) BAB16046 | (SEQ ID NO: 20) |
| *Gallus gallus* (chicken) AAK18000 | (SEQ ID NO: 21) |
| *Gallus gallus* (chicken) AAR18244 | (SEQ ID NO: 22) |
| *Homo sapiens* (human) NP-005250 | (SEQ ID NO: 8) |
| *I. punctatus* (catfish)AAK84666 | (SEQ ID NO: 23) |
| *Lepus capensis* (hare)AAN87890 | (SEQ ID NO: 24) |
| *Macaca fascicularis* (monkey) AAL17640 | (SEQ ID NO: 25) |
| *Meleagris gallopavo* (turkey)AAB86692 | (SEQ ID NO: 26) |
| *Morone chrysops* (white bass)AAK28707 | (SEQ ID NO: 27) |
| *Mus musculus* (house mouse)AAC531 67 | (SEQ ID NO: 28) |
| *O. mykiss* (trout) AAK71 707 | (SEQ ID NO: 29) |
| *Ovis aries* (sheep)AAB86689 | (SEQ ID NO: 30) |
| *Papio hamadryas* (baboon)AAB86686 | (SEQ ID NO: 31) |
| *Rattus norvegicus* (rat)AAB86691 | (SEQ ID NO: 32) |
| *Salmo salar* (salmon) CAC1 9541 | (SEQ ID NO: 33) |
| *Sparus aurata* (seabream)AAL05943 | (SEQ ID NO: 34) |
| *Sus scrofa* (pig)AAC08035 | (SEQ ID NO: 35) |
| *Sus scrofa* (pig) AAR18245 | (SEQ ID NO: 36) |

DETAILED DESCRIPTION OF THE INVENTION

Accordingly, the present invention identifies GDF8 domains that serve as a specific neutralization epitope for a polyclonal anti-GDF8 goat antiserum and for other certain specific anti-GDF8 antibodies. These epitopes also serve to provide fragments of the GDF8 protein that are useful for eliciting an active and specific immune response against GDF8 proteins, both in vitro, e.g. for detection of GDF8 protein, and in vivo, for downregulating GDF8 activity. These fragments are generally referred to herein as GDF8 peptides or peptide fragments. The utility of these GDF8 peptides includes use as immunogens for eliciting an anti-GDF8 immune response in animals, and use as highly specific antibody-binding targets in GDF8-related assays.

The specific binding epitopes of GDF8 were identified by contacting anti-GDF8 antiserum with a battery of overlapping GDF8 peptides, and determining the degree of binding activity between the peptides and the antiserum IgG antibodies. The anti-GDF8 antiserum was obtained from a goat immunized with a precursor GDF8 protein having a structure optimized for expression and antigenicity.

In order to more fully appreciate the instant invention, the following definitions are provided. The use of singular terms for convenience in description is in no way intended to be so limiting. Thus, for example, reference to a composition comprising "polypeptide" includes reference to one or more of such polypeptides.

As used herein the term "approximately" is used interchangeably with the term "about" and signifies that a value is within twenty percent of the indicated value i.e., a peptide containing "approximately" 50 amino acid residues can contain between 40 and 60 amino acid residues.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

As used herein, the term, "polypeptide" is used interchangeably with the term "protein" and denotes a polymer comprising two or more amino acids connected by peptide bonds. Preferably, unless otherwise stated herein, the term polypeptide is distinguished from the term, "peptide" as employed herein, by size or chain length, wherein a "peptide" refers to a polymer chain of about fifty or fewer amino acids, and a polypeptide or protein refers to polymer chain comprising more than about fifty amino acids. Optionally, a peptide or a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

A "GDF8 peptide" according to the present invention is a relatively short fragment derived from the GDF8 protein. Even subfragments of such peptides can be termed GDF8 peptides. While not intending to limit the maximum size of a GDF8 peptide according to the invention, it is preferred that the maximum size of the peptide is about 50 residues, more preferably the maximum size is about 40 residues, even more preferably the maximum size is about 30 residues, and still more preferably the maximum size is about 25 residues. More generally, the GDF8 peptide preferably ranges in size from about 10 to about 50 amino acid residues in length, more preferably from about 15 to about 30 amino acid residues, and in particular, is about 20 amino acid residues in length. GDF8 peptides that are smaller subfragments of other GDF8 peptides of the present invention, for example, a GDF8 peptide comprising about 10 consecutive amino acid residues from DJ5 (SEQ ID NO:8), preferably comprise an antigenic portion (e.g., an epitope) from the larger GDF8 peptide.

In a particular embodiment, a GDF8 peptide comprises a peptide domain that has a degree of homology ranging from about 50% to 100% homology to a peptide defined by residue numbers 327-346 (SEQ ID NO: 8) of the naturally occurring human precursor of GDF8 (SEQ ID NO: 1). The variations in homology noted above are preferably conservative substitutions and/or variations that retain the inventive antigenic structure that is specifically recognized by certain specific anti-GDF8 antibodies. These conserved substitutions represent residue substitutions that are shown by interspecies homology comparisons (e.g., see FIG. 2) to preserve GDF8 function and/or represent residue substitutions between amino acids of analogous chemical (e.g., physical) and electronic structure, thus preserving and/or optimizing the antibody-binding specificity of the inventive GDF8 peptides. Examples of such conservative amino acid substitutions include: replacing one hydrophobic residue such as isoleucine, valine, leucine or methionine for another; or replacing one polar residue of equivalent charge for another, e.g., substituting arginine for lysine, glutamic acid for aspartic acid, or glutamine for asparagine.

In particular, the GDF8 peptide according to the invention will also include a specific neutralization epitope for an anti-GDF8 antibody, i.e. an epitope or antigenic domain that will specifically bind to the PGA anti-GDF8 IgG polyclonal antibody described by the Examples below, and/or that binds specifically to commercially available rat monoclonal antibody ("mAb") Cat. No. MAB788 (R&D Systems Inc., Minneapolis. MN).

The terms "purified" or "isolated" as employed herein, refer to materials separated under conditions that reduce or eliminate the presence of unrelated materials, i.e., contaminants, including native materials from which the material is obtained. For example, a purified or isolated protein is preferably free of other proteins or nucleic acids with which it can be found within a cell. A purified material may contain less than about 50%, preferably less than about 75%, and most preferably less than about 90%, of the cellular components with which it was originally associated. Purity can be evaluated by chromatography, get electrophoresis, immunoassay, composition analysis, biological assay and other methods known in the art. From a functional aspect, an isolated GDF8 peptide according to the invention is one sufficiently separated from other materials, including precursor GDF8 protein and/or mature GDF8 protein, so as to be capable of eliciting an immune response that is specific for the GDF8 peptide.

Methods for purification are well-known in the art. For example, nucleic acids can be purified by precipitation, chromatography, ultracentrifugation and other means. Proteins and polypeptides, as well as peptides, can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction and countercurrent distribution. For some purposes, it is preferable to produce the polypeptide in a recombinant system in which the protein contains an additional sequence tag that facilitates purification, such as, but not limited to, a polyhistidine sequence or a sequence that specifically binds to an antibody, such as FLAG® and GST. The polypeptide can then be purified from a crude lysate of the host cell by chromatography on an appropriate solid-phase matrix. Alternatively, antibodies, or binding fragments thereof, produced against the polypeptide can be used as purification reagents.

The term "substantially pure" indicates the highest degree of purity which can be achieved using conventional purification techniques known in the art and means a nucleic acid, polypeptide, peptide, or other material that is free from other contaminating proteins, nucleic acids and other biologicals derived from an original source organism or recombinant DNA expression system. Substantial purity may be assayed by standard methods and wilt typically exceed at least about 75%, preferably at least about 90%, more preferably at least about 95% and most preferably at least about 99% purity. Purity evaluation may be made on a mass or molar basis.

A "polynucleotide" or a "nucleic acid molecule" is a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

A "vector" or "replication vector" is a replicon, such as a plasmid, phage, or cosmid, to which another DNA segment may be attached or incorporated so as to bring about the replication of the attached segment. The term also includes a replicon that includes the incorporated or attached DNA segment of interest.

Vectors that can be used in this invention include microbial plasmids, viruses, bacteriophage, integratable DNA fragments and other vehicles that may facilitate integration of the nucleic acids into the genome of the host. Plasmids are the most commonly used form of vector, but all other forms of vectors which serve an equivalent function and which are or become known in the art are suitable for use herein. See, e.g., Pouwels et al., *Cloning Vectors: A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Insertion of DNA encoding the inventive GDF8 peptide(s) into a vector is easily accomplished when the termini of both the DNA and the vector comprise compatible restriction sites. If this cannot be done, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). See, e.g., Saiki et al., *Science* 239:487 (1988). The cleaved vector and the DNA fragments may also be modified, if required, by homopolymeric tailing.

Recombinant expression vectors used in this invention are typically self-replicating DNA or RNA constructs comprising nucleic acids encoding one of the inventive GDF8 peptide(s), usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors may also contain an origin of replication that allows the vector to replicate independently of the host cell.

Expression of nucleic acids encoding inventive GDF8 peptide(s) can be carried out by conventional methods in either prokaryotic or eukaryotic cells.

A DNA "coding sequence" or a "sequence encoding" a particular protein or peptide, is a DNA sequence which is transcribed and translated into a polypeptide in vitro or in vivo when placed under the control of appropriate regulatory elements. The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

As used herein the terms "fusion protein" and "fusion peptide" are used interchangeably and encompass "chimeric proteins and/or chimeric peptides" and fusion "intein proteins/peptides". A fusion protein comprises at least a portion of a GDF8 peptide of the present invention joined via a peptide bond to at least a portion of another protein. For example, fusion proteins can comprise a marker protein or peptide, or a protein or peptide that aids in the isolation and/or purification and/or antigenicity of a GDF8 peptide of the present invention. A GDF8 fusion protein can comprise at least a portion of a non-GDF8 protein joined via a peptide bond to at least a portion of a GDF8 polypeptide. In preferred embodiments a portion of the GDF8 is functional, i.e., retains its antigenicity. The non-GDF8 sequences can be amino- or carboxy-terminal to the GDF8 sequences.

A recombinant DNA molecule encoding such a fusion protein comprises a sequence encoding at least a portion of a non-GDF8 protein joined in-frame to the GDF8 coding sequence, and can encode a cleavage site for a specific protease, e.g., thrombin or Factor Xa, preferably at or close to the juncture between the GDF8 sequence and the non-GDF8 sequence. In a specific embodiment, the fusion protein is expressed in a CHO cell. Such a fusion protein can be used to isolate the GDF8 peptides of the present invention, through the use of an affinity column that is specific for the protein and/or tag fused to the GDF8 peptide. The purified GDF8 peptide, for example, may then be released from the fusion protein through the use of a proteolytic enzyme and a cleavage site such as has been referred to above.

In one such embodiment, a chimeric GDF8 peptide can be prepared, e.g., a glutathione-S-transferase (GST) fusion protein, a maltose-binding (MBP) protein fusion protein, or a poly-histidine-tagged fusion protein, for expression in any cell, or alternatively in a cell-free system. For example, GST binds glutathione conjugated to a solid support matrix, MBP binds to a maltose matrix, and poly-histidine chelates to a Ni-chelation support matrix. The fusion protein can be eluted from the specific matrix with appropriate buffers, or by treating with a protease specific for a cleavage site usually engineered between the GDF8 peptide and the fusion partner (e.g., GST, MBP, FLAG®) as exemplified below, or poly-His as described above.

A "heterologous nucleotide sequence"[1] as used herein is a nucleotide sequence that is added to a nucleotide sequence of the present invention by recombinant methods to form a nucleic acid that is not naturally formed in nature. Such nucleic acids can encode fusion (e.g., chimeric) proteins. Thus the heterologous nucleotide sequence can encode peptides and/or proteins that contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

A "host cell" is a cell that contains, or is capable of containing, and expressing, an exogenous nucleic acid molecule, either transiently or permanently. A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

Prokaryotes include both gram negative and positive organisms, e.g. *E. coli* and *B. subtilis*. Higher eukaryotes include established tissue culture cell lines from animal cells, both of non-mammalian origin, e.g. insect cells, and birds, and mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express GDF8, and/or GDF8 peptides, include, but are not limited to, those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses,* 1988, Buttersworth, Boston, pp. 205-236.

Yeast, as well as higher eukaryotic tissue culture cells are preferred hosts for the recombinant production of the inventive GDF8 peptides, and/or of anti-GDF8 antibodies and/or fragments of those antibodies. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include, for example, an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pcDNA1, pCD [Okayama et al., *Mol. Cell Biol.* 5:1136 (1985)], pMC1neo Poly-A [Thomas et al., *Cell* 51:503 (1987)], pUC19, pREP8, pSVSPORT and derivatives thereof, and baculovirus vectors, such as pAC 373 or pAC 610.

Prokaryotic expression control sequences typically used include promoters, including those derived from the β-lactamase and lactose promoter systems [Chang et al., *Nature,* 198:1056 (1977)], the tryptophan (trp) promoter system [Goeddel et al., *Nucleic Acids Res.* 8:4057 (1980)], the lambda $P_L$ promoter system [Shimatake et al., *Nature,* 292: 128 (1981)] and the tac promoter [De Boer et al., *Proc. Natl. Acad. Sci,* USA 292:128 (1983)]. Numerous expression vectors containing such control sequences are known in the art and commercially available.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

The invention also includes polyclonal and monoclonal (mAb) antibodies that specifically bind to the inventive GDF8 peptides. As used herein, the term "antibody" refers to an immunoglobulin and/or fragments thereof. A naturally occurring immunoglobulin consists of one or more polypeptides substantially encoded by immunoglobulin genes. The recognized immunoglobulin genes include the kappa, lambda, alpha, gamma, delta, epsilon and mu constant region genes, as well as the myriad immunoglobulin variable region genes. An antibody or antibodies according to the invention also encompass antibody fragments, i.e., antigen-binding fragments, for example, Fv, Fab, and F(ab')$_2$, engineered single-chain binding proteins, (e.g., Huston et al., *Proc. Natl. Acad. Sci.* U.S.A., 85, 5879-5883 (1988) and Bird et al., *Science,* 242, 423-426 (1988), hereby incorporated herein by reference in its entireties), as well as bifunctional hybrid antibodies (e.g., Lanzavecchia et al., *Eur. J. Immunol.* 17, 105 (1987)). [See, generally, Hood et al., Immunology, Benjamin, N.Y., 2nd ed. (1984), Harlow and Lane, *Antibodies. A Laboratory Manual,* Cold Spring Harbor Laboratory (1988) and Hunkapiller and Hood, *Nature,* 323, 15-16 (1986), the contents of all of which are hereby incorporated by reference in their entireties.]

For example, serum produced from animals immunized by the inventive GDF8 peptides, using standard methods, can be used directly, or the IgG fraction can be separated from the serum using standard methods, such as plasmaphoresis or adsorption chromatography with IgG-specific adsorbents, such as immobilized Protein A or Protein G. Alternatively, monoclonal antibodies can be prepared, and optionally antigen binding fragments or recombinant binding proteins derived from such mAbs. Such MAbs or fragments thereof can optionally be humanized by art-known methods.

Hybridomas producing mAbs that selectively bind the GDF8 peptides of the invention, are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and, in general, involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay) or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al. *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982]. Monoclonal antibodies can also be produced using well-known phage library systems. See, e.g., Huse, et al., *Science* 246:1275 (1989); Ward, et al., *Nature,* 341:544 (1989).

Antibodies thus produced, whether polyclonal or monoclonal, can be used, e.g., in an immobilized form bound to a solid support by well known methods to purify the GDF8 peptides by immunoaffinity chromatography.

Antibodies against the GDF8 peptides can also be used, unlabeled or labeled by standard methods, as the basis for immunoassays to detect or quantify GDF8. The particular label used will depend upon the type of immunoassay. Examples of labels that can be used include, but are not limited to, radiolabels, such as $^{32}P$, $^{125}I$, $^{3}H$ and $^{14}C$; fluorescent labels, such as fluorescein and its derivatives, rhodamine and its derivatives, dansyl and umbelliferone; chemiluminescers, such as luciferia and 2,3-dihydrophthalazinediones; and enzymes, such as horseradish peroxidase, alkaline phosphatase lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing GDF8-related polypeptides in expression cloning systems. Neutralizing antibodies specific for the ligand-binding site of a receptor can also be used as antagonists (inhibitors) to block or down-regulate GDF8 function. Such neutralizing antibodies can readily be identified through routine experimentation, as exemplified by the Examples provided below.

Antagonism of GDF8 activity can be accomplished using complete antibody molecules, or well-known antigen binding fragments such as Fab, Fc, F(ab)$_2$, and Fv fragments. Definitions of such fragments can be found as described hereinabove, or e.g. in Klein, *Immunology* (John Wiley, New York, 1982); Parham, Chapter 14, in Weir, ed. *Immunochemistry,* 4th Ed, (Blackwell Scientific Publishers, Oxford, 1986). The use and generation of antibody fragments has also been described, e.g.: Fab fragments [Tijssen, *Practice and Theory of Enzyme Immunoassays* (Elsevier. Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described. e.g. by Moore et al. (U.S. Pat. No. 4,642,334) and by Plückthun [*Bio/Technology* 9:545 (1991)]. Alternatively, they can be chemically synthesized by standard methods.

The present invention also encompasses anti-idiotypic antibodies, both polyclonal and monoclonal, which are produced using the above-described antibodies as antigens. These antibodies are useful because they may mimic the structures of the ligands.

Peptide Synthesis

Since the inventive GDF8 peptides, e.g., the DJ5 peptide exemplified hereinbelow, are relatively short (e.g., preferably 50 amino acid residues or less), they may be prepared by art-known methods of peptide synthesis. Synthetic peptides or polypeptides, prepared using the well-known techniques of solid phase, liquid phase, or peptide condensation techniques, or any combination thereof, can include natural and unnatural amino acids. Amino acids used for peptide synthesis may be standard Boc ($N_{alpha}$-amino protected $N_{alpha}$-t-butyloxycarbonyl) amino acid resin with the standard deprotecting, neutralization, coupling and wash protocols of the original solid phase procedure of Merrifield [*J. Am. Chem. Soc.,* 85:2149-2154 (1963)], or the base-labile $N_{alpha}$-amino protected 9-fluorenylmethoxycarbonyl (Fmoc) amino acids first described by Carpino and Han [*J. Org. Chem.,* 37:3403-3409 (1972)]. Both Fmoc and Boc $N_{alpha}$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N_{alpha}$-protecting groups that are familiar to those skilled in this art. Solid phase peptide synthesis may be accomplished by techniques familiar to those in the art and provided, for example, in Stewart and Young, SOLID PHASE SYNTHESIS, Second Edition, Pierce Chemical Co., Rockford, Ill., (1984); Fields and Noble, *Int. J. Pept. Protein Res.* 35:161-214 (1990), or using automated synthesizers, such as sold by ABS [Applied Biosystems, 850 Lincoln Centre Drive, Foster City, Calif. 94404 USA]. Thus, the GDF8 peptides of the invention may comprise D-amino acids, a combination of D- and L-amino acids, and various "designer" amino acids (e.g., beta-methyl amino acids, $C_{alpha}$-methyl amino acids, and $N_{alpha}$-methyl amino acids, etc.) to convey special properties. Synthetic amino acid include ornithine for lysine, fluorophenylalanine for phenylalanine, and norleucine for leucine or isoleucine. Additionally, by assigning specific amino acids at specific coupling steps, alpha-helices, beta turns, beta sheets, gamma-turns, and cyclic peptides can be generated.

Anti-GDF8 Antiserum

The methods of the invention included a process of screening GDF8 peptides against a polygonal anti-GDF8 antiserum. This process identified the epitope that certain anti-GDF8 antibodies bind to in a highly specific way. The anti-GDF8 antiserum was obtained by immunizing an animal with precursor GDF8. The precursor GDF8 gene was modified to provide a form optimized for expression and immunogenicity. For example, the natural DNA sequence of the GDF8 prohormone (SEQ ID NO: 2) was optimized for expression in mammalian and viral expression systems. In addition, changes were made to avoid the negative effects of viral host shutoff mechanisms. Typically viral host shutoff mechanisms involve transcriptional control, RNA stability (splicing) and such. These changes made the nucleic acid less host like and more virus like.

Further, the DNA sequence was preferably designed to be as divergent from the mammalian nucleic acid sequence as possible. For example, the amino acid sequence of the precursor GDF8 was reverse translated using yeast preferred codons. The resulting sequence was surveyed for codons that retained their homology to the human GDF8 nucleic acid sequence. Where possible these codons were substituted with the next most preferred yeast codons encoding the same amino acid.

The resulting optimized gene (SEQ ID NO: 3) can be expressed in any suitable host system, including, e.g., art-known insect, mammalian, bacterial, viral and yeast expression systems. For example, insect cell expression systems, such as baculovirus systems, are art-known and described, for instance, by Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit). Similarly, bacterial and mammalian cell expression systems are well known in the art and described, for example, by Sambrook et al. (MOLECULAR CLONING: A LABORATORY MANUAL; DNA Cloning, Vols. I and II; D. N. Glover ed.). Yeast expression systems are also known in the art and described, for example, by, YEAST GENETIC ENGINEERING (Barr et al., eds., 1989) Butterworths, London. Many other such expression systems are known to the art and are available commercially in kit form. As exemplified herein, the modified precursor GDF8 gene (SEQ ID NO: 3) was expressed in a Flp-In™ CHO expression system (invitrogen, Carlsbad, Calif.) as described in greater detail by Example 1, below.

The precursor GDF8 protein, as well as peptides of the mature GDF8 protein, can be incorporated into any protein- or peptide-compatible vaccine composition. Such vaccine compositions are well known to the art and include, for example, physiologically compatible buffers and saline and the like, as well as adjuvants, as described in greater detail hereinbelow. The vaccine composition including the precursor GDF8 protein is employed for eliciting antiserum for screening and identifying a specific neutralization epitope for an anti-GDF8 antibody.

As exemplified herein, purified precursor GDF8 protein expressed by a vector comprising SEQ ID NO:3 was injected into a goat in a vaccine composition that included 1 g of precursor GDF8 protein emulsified into Freund's complete adjuvant (CFA). The vaccine composition was preferably injected subcutaneously (SC) beneath the skin of the goat. Subsequent booster immunizations are preferred. These can be administered at suitable additional intervals with the same or a reduced dosage of the protein, e.g., at intervals ranging from 2-5 weeks after the initial injection.

Beginning from about two weeks after the initial injection, but preferably starting after a longer time period, e.g., from three to fifteen weeks, or longer, serum is collected, as needed, from the immunized animal. The collected serum is then preferably purified and/or fractionated by conventional immunoglobulin purification procedures such as, for example, protein A-Sepharose, protein G-agarose, hydroxylapatite chromatography, gel electrophoresis, dialysis, or affinity chromatography with a suitable ligand. As exemplified herein, the IgG fraction of the serum was further fractionated on a protein G-agarose column.

The anti-GDF8 antiserum IgG fraction is then available for screening against a range of peptides of the mature GDF8, as described in greater detail by Example 3, hereinbelow.

GDF8 Binding Epitopes

Suitable anti-GDF8 monoclonal or polyclonal antibodies were contacted with GDF8 protein for a time period sufficient for the antibody to bind selectively to the protein. Thereafter, GDF8 bioassays conformed that the antibody neutralized substantially all of the GDF8 protein activity. Any GDF8 bioassay can be employed for this purpose, although, as exemplified hereinbelow by Example 3, an in vitro transcriptional activation assay according to Thies et. al., 2001, (*Growth Factors* 18, 251) is preferred.

Generally, a GDF8 peptide useful as an antigen or binding epitope according to the invention includes from about residue 312 to about residue 361 of GDF8 (SEQ ID NO: 1). In particular, a peptide according to the invention includes from about residue 320 to about residue 350 of GDF8 (SEQ ID NO: 1). The peptide preferably includes from about residue 327 to about residue 346 of GDF8 (SEQ ID NO: 1).

The artisan will appreciate that the inventive GDF8 peptide can be readily modified to include at least one conservative amino acid substitution, and at any position. Preferably, that peptide specifically binds to rat monoclonal antibody 788, as exemplified hereinbelow. Such conservative substitutions can include, for example, variations at residues 328, 329 and 335, and combinations thereof, wherein, amino acid residue 328 is His, Leu, Asn or Val, amino acid residue 329 is Lys or Leu; and amino acid residue 335 is Ser or Pro or Thr. Precursor GDF8 residues 328, 329 and 335 vary within the GDF8 protein sequence across species, as illustrated by FIG. 2, but nevertheless, the mature GDF8 remains functional.

FIG. 1 illustrates a map of the GDF8 active region (that forms the mature protein) in the context of its precursor protein. Superimposed on the map of the GDF8 active region are the locations of seven overlapping peptides. These overlapping peptide were designed in order to provide targets for identifying the antibody-binding epitope or epitopes of GDF8. The peptide labeled as DJ5 was identified by screening with the IgG fraction of the exemplified goat anti-GDF8 antiserum as the only significant binding epitope of GDF8 for the exemplified antiserum. This peptide has a sequence (SEQ ID NO: 8) corresponding to residue 327 to residue 346 of precursor GDF8 (SEQ ID NO: 1).

GDF8 Peptide Vaccine Compositions

The GDF8 peptides described above are preferably formulated into vaccine compositions. These vaccine compositions may be employed to immunize an animal in order to elicit a highly specific anti-GDF8 immune response. The result of the immunization will be downregulation of GDF8 function in the immunized animal.

Such vaccine compositions are well known to the art and include, for example, physiologically compatible buffers, preservatives, and saline and the like, as well as adjuvants.

"Adjuvants" are agents that nonspecifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate and alum; surfactants, such as hexadecylamine, octadecylamine, lysolecithin, dimethyldioctadecylammonium bromide, N,N-dioctadecyl-N',N'-bis (2-hydroxymethyl) propanediamine, methoxyhexadecylglycerol and pluronic polyols; polyanions, such as pyran, dextran sulfate, poly IC, polyacrylic acid and carbopol; peptides, such as muramyl dipeptide, dimethylglycine and tuftsin; and oil emulsions. The protein or peptides could also be administered following incorporation into liposomes or other microcarriers. Information concerning adjuvants and various aspects of immunoassays are disclosed, e.g., in the series by P. Tijssen, *Practice and Theory of Enzyme Immunoassays,* 3rd Edition, 1987, Elsevier, New York, incorporated by reference herein.

The vaccine composition includes a sufficient amount of the desired immunogen, such as the inventive GDF8 peptides, to elicit an immune response. The amount administered can range from about 0.0001 g/kg to about 1.0 g/kg, relative to the mass of the animal. Any suitable vertebrate animal is readily employed to obtain polyclonal antiserum. Preferably, the animal is a mammal, and includes, but is not limited to, rodents, such as mice, rats, rabbits, horses, canines, felines, bovines, ovines, e.g., goats and sheep, primates, e.g., monkeys, great apes and humans, and the like.

The vaccine composition is readily administered by any standard route, including intravenously, intramuscularly, subcutaneously, intraperitoneally, in ovo (particularly for poultry), and/or orally, For fish species, methods of administering a vaccine composition or immunogenic composition include the foregoing, as well as dipping the fish into water comprising an antigenic concentration of the peptide, spraying the fish with an antigenic concentration of the peptide while the fish is briefly separated from the water, etc. The artisan will appreciate that the vaccine composition is preferably formulated appropriately for each type of recipient animal and route of administration.

Appropriate animal subjects can include those in the wild, livestock (e.g., raised for meat, milk, butter, eggs, fur, leather, feathers and/or wool), beasts of burden, research animals, companion animals, as well as those raised for/in zoos, wild habitats and/or circuses. In a particular embodiment, the animal is a great ape such as a gorilla, or a human.

In one preferred embodiment, the animal is a "food-producing" animal, and the result of immunization is a gain in animal weight, particularly muscle mass, relative to animals not immunized. For purposes of the present invention, the term "food-producing" animal shall be understood to include all animals bred for consumption by humans and/or other animals, or for producing consumables such as eggs or milk. A non-limiting list of such animals include avians (e.g., chickens, turkeys, ducks, geese, ostriches), bovine (e.g., beef/veal cattle, dairy cows, breeding bulls, buffalo), porcine (e.g., hogs or pigs), ovine (e.g., goats or sheep), equine (e.g., horses) as well as aquatic animals, including shellfish and fish such as trout or salmon, and other species raised or harvested for human consumption.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping.

Examples of potential fish recipients include the Salmonidae family, the Serranidae family, the Sparidae family, the Cichlidae family, the Centrarchidae family, the three-Line Grunt (*Parapristipoma trilineatum*), and the Blue-Eyed *Plecostomus* (*Plecostomus* spp).

| *Salmonidae* Family | |
|---|---|
| TAXON NAME | COMMON NAME |
| *Coregonus clupeaformis* | Lake whitefish |
| *Coregonus hoyi* | Bloater |
| *Oncorhynchus keta* | Chum salmon |
| *Oncorhynchus gorbuscha* | Pink salmon |
| *Oncorhynchus kisutch* | Coho salmon (silver salmon) |
| *Oncorhynchus masou* | cherry salmon (masou salmon) |
| *Oncorhynchus nerka* | Sockeye salmon |
| *Oncorhynchus tshawytscha* | (chinook salmon) |
| *Prosopium cylindraceum* | Round whitefish |
| *Oncorhynchus clarki* | Cutthroat trout |
| *Oncorhynchus mykiss* | Rainbow trout |
| *Salmo salar* | Atlantic salmon |
| *Salmo trutta* | Brown trout |
| *Salmo trutta* X *S. fontinalis* | Tiger hybrid-trout |
| *Salvelinus alpinus* | Arctic charr |
| *Salvelinus confluentus* | Bull trout |
| *Salvelinus fontinalis* | Brook trout |
| *Salvelinus leucomaenis* | Japanese charr (white spotted charr) |
| *Salvelinus malma* | Dolly varden (Miyabe charr) |
| *Salvelinus namaycush* | Lake trout |
| *Thymallus thymallus* | Grayling |

| Some Members of the *Serranidae* Family | |
|---|---|
| TAXON NAME | COMMON NAME |
| *Centropristis ocyurus* | Bank sea bass |
| *Centropristis philadelphicus* | Rock sea bass |
| *Centropristis striata* | Black sea bass |
| *Diplectrum bivittatum* | Dwarf sandperch |
| *Diplectrum formosum* | Sand perch |
| *Epinephelus flavolimbatus* | Yallowedge grouper |
| *Epinephelus morio* | Red grouper |
| *Serranus phoebe* | Tattler |
| *Serranus tortugarum* | Chalk bass |

| Some Members of the *Sparidae* family | |
|---|---|
| TAXON NAME | COMMON NAME |
| *Archosargus probatocephalus* | Sheepshead |
| *Archosargus rhomboidalis* | Sea bream |
| *Calamus penna* | Sheepshead porgy |
| *Lagodon rhomboides* | Pinfish |
| *Pagrus Major* | Red Sea bream |
| *Sparus aurata* | Gilthead Sea bream |
| *Stenotomus chrysops* | Scup |

Some Members of the *Cichlidae* family

| TAXON NAME | COMMON NAME |
| --- | --- |
| *Aequidens latifrons* | Blue acara |
| *Cichlisoma nigrofasciatum* | Congo cichlid |
| *Crenichichla* sp. | Pike cichlid |
| *Pterophyllum scalare* | Angel fish |
| *Tilapia mossambica* | Mozambique mouth breeder |
| *Oreochromis* sp. | Tilapia |
| *Sarotherodon aurea* | Golden Tilapia |

Some Members of the *Centrarchidae* family

| TAXON NAME | COMMON NAME |
| --- | --- |
| *Ambloplites rupestris* | Rock bass |
| *Centrarchus macropterus* | Flier |
| *Elassoma evergladei* | Everglades pigmy sunfish |
| *Elassoma okefenokee* | Okefenokee pigmy sunfish |
| *Elassoma zonatum* | Banded pigmy sunfish |
| *Enneacanthus gloriosus* | Bluespotted sunfish |
| *Enneacanthus obesus* | Banded sunfish |
| *Lepomis auritus* | Redbreast sunfish |
| *Lepomis cyanellus* | Green sunfish |
| *Lepomis cyanellus* X *L. gibbosus* | Green x pumpkinseed |
| *Lepomis gibbosus* | Pumpkinseed |
| *Lepomis gulosus* | Warmouth |
| *Lepomis humilis* | Orange-spotted sunfish |
| *Lepomis macrochirus* | Bluegill |
| *Lepomis megalotis* | Longear sunfish |
| *Micropterus coosae* | Shoal bass |
| *Micropterus dolomieui* | Smallmouth bass |
| *Micropterus punctulatus* | Spotted bass |
| *Micropterus salmoides* | Largemouth bass |
| *Pomoxis annularis* | White crappie |
| *Pomoxis nigromaculatus* | Black crappie |

In a further preferred embodiment, the animal is a companion animal or a human, and the vaccine is administered to provide long-term downregulation of GDF8 for any veterinary or medical purpose responsive to such GDF8 downregulation. For purposes of the present invention, the term "companion" animal shall be understood to include all animals—horses (equine), cats (feline), dogs (canine), rodents, (including mice, rats, guinea pigs), rabbit species, and avians, such as pigeons, parrots and the like.

Other birds receiving such vaccination or antibodies can be associated with either commercial or noncommercial aviculture. These include e.g., Anatidae, such as swans, Columbidae, e.g., doves and pigeons, such as domestic pigeons, Phasianidae, e.g., partridge, and grouse, Thesienidae, Psittacines, e.g., parakeets, macaws, and parrots, e.g., raised for the pet or collector market, and members of the Ratite family.

In another preferred embodiment, any of the above recited animals (preferably nonhuman) are immunized in order to obtain anti-GDF8 antibodies that specifically bind to the inventive peptides, and the elicited antibodies are harvested for use in assays, and/or in veterinary or human medicine, e.g., to provide downregulation of GDF8 for any veterinary or medical purpose responsive to such GDF8 downregulation.

The present invention may be better understood by reference to the following non-limiting examples, which are provided as exemplary of the invention. The following examples are presented in order to more fully illustrate embodiments of the invention and should in no way be construed as limiting the broad scope of the invention.

EXAMPLES

Example 1

Materials & Methods

A. Expression and Purification of Precursor GDF8 (GDF8 Prohormone)

The natural DNA sequence of the precursor GDF8 or prohormone (SEQ ID NO: 2) was optimized for expression in mammalian and viral expression systems. To avoid the negative effects of viral host shutoff mechanisms the DNA sequence was designed to be as divergent from the mammalian nucleic acid sequence as possible. To accomplish this the amino acid sequence of the GDF8 prohormone was reversed translated using yeast preferred codons. The resulting sequence was surveyed for codons, which retained their homology to the human GDF8 nucleic acid sequence. Where possible these codons were substituted with the next most preferred yeast codons encoding the same amino acid. The resulting nucleic acid molecule (SEQ ID NO: 3) was commercially synthesized for incorporation into the appropriate expression vectors.

The Flp-In™ CHO expression system (Invitrogen, Carlsbad, Calif.) was used to express the optimized GDF8 prohormone. Briefly, a GDF8 prohormone construct containing a C-terminal FLAG® (Sigma-Aldrich Corp., St Louis, Mo.) epitope fusion was constructed by inserting the gene encoding the modified GDF8 prohormone into plasmid pCMVtag4B (Stratagene, San Diego, Calif.). The FLAG® fusion tag facilitates separation of FLAG® fusion proteins on an anti-FLAG® gel column. A PCR DNA fragment containing the modified GDF8 prohormone-FLAG® gene was then cloned into plasmid expression vector pcDNA5/FRT (Invitrogen, Carlsbad, Calif.). Generation of the Flp-In™ CHO cell line expressing the GDF8 prohormone-FLAG® fusion protein was achieved by cotransfection of the Flp-In™ CHO cell line with the Flp-In™ expression vector containing the GDF8-FLAG® gene and the Flp recombinase expression plasmid, POG44. Ftp recombinase mediates insertion of the Flp-In expression cassette into the genome at an integrated FRT site by site-specific DNA recombination. A stable cell line expressing and secreting the GDF8 prohormone containing the FLAG® epitope was obtained using hygromycin B selection.

The stable CHO cell line expressing the GDF8 prohormone containing the FLAG® tag was adapted to suspension culture in serum-free media using standard techniques. Conditioned media containing the secreted GDF8 prohormone was generated using the WAVE bioreactor system (WAVE Biotech LLC, Bridgewater, N.J.). Purification of the FLAG® tagged GDF8 prohormone was achieved by affinity chromatography using an anti-FLAG® M2 affinity gel (Sigma-Aldrich Corp., St. Louis, Mo.).

B. DJ5 Specific Antibody Purification

DJ5 (SEQ ID NO: 8; See Table 2, below) specific antibody fractions were purified by affinity column chromatography. An affinity column was prepared by coupling 10 mg of DJ5 synthetic peptide to 0.8 g of cyanogen bromide-activated Sepharose 4B (Sigma Genosys, Woodlands, Tex.). The column was washed and equilibrated with PBS. Approximately 11 ml of Goat IgG fraction (10 mg/ml) was applied to the affinity column and washed with 25 ml of PBS. Fractions of 1.0 ml were collected and monitored for absorbance at 280 nm. Bound material was eluted with approximately 10 ml of 0.2 M glycine (pH 1.85). Fractions of 1.0 ml were collected and neutralized with 0.25 ml of 0.5 M sodium phosphate, 0.75

M NaCl, pH 7.4. Approximately 25 μl aliquots of unbound fractions 1-10 and bound fractions 25-35 were assayed for ELISA reactivity to DJ5 peptide. Unbound fractions were found to be negative for DJ5 reactivity. Bound fractions exhibited a strong peak of reactivity to the DJ5 peptide. Unbound fractions 1-11 and bound fractions 26-34 were pooled. Pooled samples were concentrated and their buffer exchanged with phosphate buffered saline (PBS) as indicated below. Sample concentrations were determined by the OD 280 method (CURRENT PROTOCOLS IN IMMUNOLOGY, 2.7.3, John Wiley & Sons, Inc.). The unbound sample was adjusted to 10 mg/ml and the bound sample was adjusted to 1 mg/ml, for subsequent use.

Example 2

Goat Anti-GDF8 Polyclonal IgG Serum

Goat anti-precursor GDF8 IgG was obtained from an immunized goat by the following methods.

A. Immunization of Goat

A Saanen (dairy) goat (approximately 2 year old male) was immunized with purified recombinant GDF8 prohormone (obtained as described by Example 1, above), as follows. One half mg of protein was emulsified in Freund's complete adjuvant (CFA) and injected subcutaneously (SC) beneath the skin of the goat. Subsequent booster immunizations administered SC at weeks three, six, and ten contained 0.3 mg of protein emulsified in Freund's incomplete adjuvant (IFA). Blood was collected from the jugular vein with a syringe and needle, and taken with vacuum bottle and tubing. The blood was collected in bottles containing anticoagulant and centrifuged at 2500 RPM for 20 minutes to remove the red blood cells. The plasma was re-calcified to produce serum. The serum sample collected 15 weeks post initial immunization was used for further analysis.

B. Collection and Purification of Goat Polyclonal IgG

Serum was harvested from the goat after 15 weeks, and the IgG fraction was purified from this serum, as follows. The IgG fraction of goat sera was purified on a Protein G agarose column according to the manufactures protocol (Kirkegaard and Perry Laboratories, Inc., Gaithersburg, Md.). Eluted fractions were pooled, concentrated, and buffer exchanged with phosphate buffered saline (PBS) utilizing Centriprep centrifugal Filters (Centriprep YM-10, Millipore Corporation, Billerica, Mass.). Sample concentrations were determined by the OD 280 method (CURRENT PROTOCOLS IN IMMUNOLOGY, Id.) and adjusted to 10 mg/ml.

Example 3

Characterization of Goat Antiserum

The goat antiserum provided by Example 2, above, is designated as PGA. It is expected that the PGA IgG fraction contains antibodies directed against various epitopes on the GDF8 prohormone molecule. The PGA antiserum was characterized by an in vitro transcription activation assay, as follows. The in vitro transcriptional activation assay used to quantitatively measure GDF8 bio-neutralization is essentially that of Thies et. al. (Growth Factors 18, 251 (2001)). Ninety-six well tissue culture treated luminometer ViewPlate™ assay plates (PerkinElmer Life and Analytical Sciences, Inc., Boston, Mass.) were seeded with $1.0 \times 10^5$ cells/well of A204 Rhabdomyosarcoma cells (ATCC HTB-82) and incubated in a 37° C., 5% CO2, humidified chamber. Complete A204 culture media consists of McCoy's 5A medium, 10% fetal bovine serum, 2% L-glutamine, and 1% Penn/Strep. Upon reaching greater than 80% confluence, the cells were transiently transfected with a mixture of plasmid pDPC4-luciferase and HCMV IE-lacZ using the protocol recommended by the manufacturer of the FUGENE transfection reagent (Roche Diagnostics Corporation, Indianapolis, Ind.) and incubated 16 hours in a 37° C., 5% CO2, humidified chamber. Plasmid pDPC4-luciferase contains four copies of the CAGA box, derived from the human plasminogen activator inhibitor (PAI-1), which confers GDF8 responsiveness to the heterologous promoter reporter construct.

Plasmid HCMV IE-lacZ contains a beta-galactosidase gene under the control of the constitutive human cytomegalovirus immediate early promoter. This gene is added as a control to normalize for transfection efficiencies. Cells were then treated with 100 ng/well GDF8 protein (R&D Systems Inc., Minneapolis, Minn.) and incubated an additional 16 hours in a 37° C., 5% CO2, humidified chamber. Luciferase and beta-galactosidase were quantified in the treated cells using the Dual-Light Luciferase Assay (Tropix, Applied Biosystems, Foster City, Calif.).

Each sample was run in duplicate (2 wells). The signal for each well was calculated as the luciferase signal divided by the beta-glactosidase signal times 100. The sample signal was calculated as the average of the two wells.

To test the bio-neutralization activity of an antibody sample various concentrations of purified IgG fractions were incubated with the GDF8 protein (approximately 16 hours at 4° C.) prior to treatment of the cells. The percent inhibition was calculated as 100−(100× sample signal)/(signal with GDF8 alone−signal with no GDF8 added). The results of the in vitro transcription activation assay are summarized by Table 1, below.

TABLE 1

GDF8 neutralization titers for Goat Serum PGA

| Sample (μg IgG) | % Inhibition of GDF8 Activity |
| --- | --- |
| Goat - normal (250) | 0 |
| Goat - PGA (250) | 95 |
| Goat - PGA (125) | 86 |
| Goat - PGA (63) | 62 |
| Goat - PGA (31) | 22 |
| Goat - PGA (16) | 3 |

The neutralization assay confirmed that the IgG fraction of the harvested goat serum contains antibodies capable of neutralizing at least 95% of the GDF8 used in this activity assay.

Example 4

Goat Polyclonal Antibody Defines a Specific Neutralization Epitope of the GDF8 Protein In order to determine the specificity of the neutralizing immune response the PGA IgG fraction was assayed for its reactivity with a set of seven overlapping peptides (DJ1-7 see Table 2 and FIG. 1) that span the entire coding region of the active GDF8 protein. Reactivity of the Goat PGA IgG to each individual peptide was determined by Enzyme-Linked immunosorbant Assay (ELISA) assay. The GDF8 peptide ELISA was performed essentially as described in Protein Detector™ ELISA Kit HRP, ABTS System (Kirkegaard and Perry Laboratories, Inc., Gaithersburg, Md.). The following modifications were used in the assay. Synthetic peptides DJ1-7 (see Table 2, below) were custom synthesized under our direction by ProSci, Inc. (Poway, Calif.). Plates were coated with synthetic peptides at 500 ng per well and purified GDF8 prohormone at 250 ng per well. Primary antibodies were IgG fractions from various samples. Secondary antibodies were used at a dilution of 1:2000. For goat primary antibody samples the secondary antibody was rabbit peroxidase-labeled antibody to goat IgG. For rat primary antibody samples the secondary antibody was goat peroxidase-labeled antibody to rat IgG. The OD 405 nm was read or 15 minutes with an ELISA plate reader. The ELISA reactivity was calculated as OD 405 per minute times 1000.

TABLE 2

GDF8 Active Region Peptides

| Name | Coordinates* | Amino acid sequence | |
|---|---|---|---|
| DJ1 | 267-286 | DFGLDCDEHSTESRCCRYPL | SEQ ID NO: 4 |
| DJ2 | 282-301 | CRYPLTVDFEAFGWDWIIAP | SEQ ID NO: 5 |
| DJ3 | 297-316 | WIIAPKRYKANYCSGECEFV | SEQ ID NO: 6 |
| DJ4 | 312-331 | ECEFVFLQKYPHTHLVHQAN | SEQ ID NO: 7 |
| DJ5 | 327-346 | VHQANPRGSAGPCCTPTKMS | SEQ ID NO: 8 |
| DJ6 | 342-361 | PTKMSPINMLYFNGKEQIIY | SEQ ID NO: 9 |
| DJ7 | 357-375 | EQIIYGKIPAMVVDRCGCS | SEQ ID NO: 10 |

*relative to Human GDF8 prohormone (Genebank Accession Number NP_005250)

The ELISA results are summarized by Table 3, below.

TABLE 3

ELISA reactivity of PGA IgG (10 mg/ml) to GDF8 Active Region Peptides

| | OD 405/ minute × 1000 | | |
|---|---|---|---|
| Antigen | 1:20 | 1:40 | 1:80 |
| DJ1* | 23 | 10 | 1 |
| DJ2* | 3 | 0 | 0 |
| DJ3* | 0 | 10 | 0 |
| DJ4* | 3 | 0 | 0 |
| DJ5* | 121 | 37 | 27 |
| DJ6* | 3 | 0 | 0 |
| DJ7* | 10 | 1 | 0 |
| proGDF8** | 194 | 196 | 199 |

*peptide,
**prohormone

The PGA IgG fraction reacted specifically with both the purified GDF8 prohormone and with the DJ5 peptide. Among the GDF8 active region peptides the IgG fraction reacts specifically and exclusively with the DJ5 peptide. This is a strong indication that the neutralizing capability of this serum is directed against an epitope defined by the DJ5 peptide. In order to confirm this hypothesis the DJ5 specific fraction of PGA IgG was purified. This was accomplished by affinity chromatography as described in the materials and methods. The PGA antibodies were separated into DJ5 peptide bound and unbound fractions. Both fractions were assayed for neutralization activity against the GDF8 protein.

The results in Table 4 show that the majority of GDF8 neutralization capacity resides with the antibody that binds specifically to the DJ5 peptide. This clearly demonstrates that the DJ5 peptide defines a neutralizing epitope of the GDF8 protein.

TABLE 4

GDF8 neutralization activity of DJ5 specific antibodies

| Sample (µg IgG) | % Inhibition of GDF8 Activity |
|---|---|
| Goat-normal (250)** | 7 |
| DJ5 unbound IgG (250) | 26 |
| DJ5 bound IgG (25) | 90 |

**The normal goat IgG was a negative control purified from non-immunized goat sera (commercially purchased).

Curiously, in a preliminary experiment, neutralizing GDF8 antibodies were not obtained when two rabbits were injected with the human DJ5 antigen conjugated to keyhole limpet hemocyanin. As can be seen in FIG. 2, the amino acid sequences corresponding to DJ5 for rabbit and human GDF8 are identical, whereas the amino acid sequence of goat DJ5 is different. Therefore, in view of the data provided above for the goat, the preliminary rabbit data suggests that it may be advantageous to use a DJ5 antigen that comprises a different amino acid sequence than that for the corresponding region/portion of the host animal GDF8. Thus, in this case, the ability of the recombinant human GDF8 prohormone to induce bio-neutralizing antibodies in a goat may be due, at least in part, to the fact that the antigen used comprised an amino acid sequence that differs from that of the host sequence by a single amino acid substitution in the DJ5 region/portion of GDF8 [see, amino acid residue 333 in FIG. 2]. More particularly, as FIG. 2 shows, the $Arg_{333}$ in the human sequence is replaced by a $Lys_{333}$ residue in the goat sequence. This lone conservative amino acid substitution may constitute an alteration that is significant enough to render the protein "foreign" to the goat immunological surveillance system.

Example 5

GDF8 Neutralizing Rat mAB 788 Defines a Specific Neutralization Epitope of the GDF8 Protein Rat monoclonal antibody 788 is reported to neutralize mouse GDF8 bioactivity (R&D Systems Inc., Cat. No. MAB788, Minneapolis, Minn.). In order to confirm this result we assayed the monoclonal antibody for neutralization activity against the GDF8 protein. The antibody was characterized as described by Example 2, above. The results of this assay are summarized by Table 5, as follows.

TABLE 5

GDF8 neutralization titers for monoclonal antibody 788

| Sample (µg IgG) | % Inhibition of GDF8 Activity |
|---|---|
| MAB-788 (12.5) | 47 |
| MAB-788 (6.3) | 17 |
| MAB-788 (3.1) | 7 |
| MAB-788 (1.8) | 0 |
| MAB-788 (0.1) | 0 |

Table 5 confirms that this antibody is capable of neutralizing the activity of the GDF8 protein. In order to determine the specificity of this neutralizing immune response the rat monoclonal antibody was assayed for its reactivity with a set of seven overlapping peptides (DJ1-7 see table 2 and FIG. 1)

that span the entire coding region of the active GDF8 protein. Reactivity of the monoclonal antibody to each individual peptide was determined by ELISA assay (see materials and methods).

TABLE 6

ELISA reactivity of Rat MAB 788 (10 mg/ml) to GDF8 active region peptides

| Antigen | OD 405/ minute × 1000 | | |
|---|---|---|---|
| | 1:20 | 1:40 | 1:80 |
| DJ1* | 4 | 0 | 0 |
| DJ2* | 0 | 0 | 0 |
| DJ3* | 0 | 0 | 0 |
| DJ4* | 0 | 0 | 0 |
| DJ5* | 133 | 118 | 102 |
| DJ6* | 0 | 0 | 0 |
| DJ7* | 0 | 0 | 0 |
| proGDF8** | 132 | 127 | 132 |

*peptide,
**protein

The rat monoclonal antibody reacted specifically with both the purified GDF8 prohormone and with the DJ5 peptide. Typically a monoclonal antibody has mono specificity to a single epitope. Among the GDF8 active region peptides this monoclonal antibody reacts specifically and exclusively with the DJ5 peptide. This result provides further independent evidence that the DJ5 peptide defines a neutralizing epitope of the GDF8 protein.

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled. Numerous references are cited in the specification, including Genebank accession numbers of published and/or internet-published nucleic acid and polypeptide/protein sequences, the disclosures of which are incorporated by reference in their entireties.

The invention claimed is:

1. A nucleic acid molecule that encodes a fusion protein, said nucleic acid molecule comprising (i) a nucleotide sequence that encodes a peptide consisting of 50 or fewer amino acid residues that comprises amino acid residues 327 to 346 of SEQ ID NO:1 and (ii) a heterologous nucleotide sequence.

2. A vector comprising the nucleic acid molecule of claim 1.

3. A host cell comprising the vector of claim 2.

4. The host cell of claim 3 that is a eukaryotic cell.

5. A method of producing a fusion protein comprising the steps of culturing the host cell of claim 3, and expressing the encoded fusion protein.

6. The method of claim 5, further comprising the step of recovering the fusion protein.

7. A nucleic acid molecule that encodes a peptide consisting of 50 or fewer amino acid residues that comprises amino acid residues 327 to 346 of SEQ ID NO:1 comprising one or more amino acid substitutions;
   wherein there are no more than five amino acid substitutions between amino acid residues 327 to residue 346; and
   wherein the peptide specifically binds to rat monoclonal antibody 788.

8. The nucleic acid of claim 7 wherein the peptide comprises amino acid substitutions at a position selected from the group consisting of residues 328, 329, 331, 333 and 335, and combinations thereof, wherein,
   (a) amino acid residue 328 is His, Leu, or Asn;
   (b) amino acid residue 329 is Gln or Lys;
   (c) amino acid residue 331 is Asn or Ser;
   (d) amino acid residue 333 is Arg or Lys; and/or
   (e) amino acid residue 335 is Ser, Pro, or Thr.

9. The nucleic acid of claim 8 wherein the peptide comprises no more than one amino acid substitution between residues 327 to residue 346 of the precursor GDF8.

10. A vector comprising the nucleic acid molecule of claim 7.

11. A nucleic acid molecule that encodes a peptide consisting of 50 or fewer amino acid residues that comprises amino acid residues 327 to 346 of SEQ ID NO:1.

12. The nucleic acid molecule of claim 11 that comprises a nucleic acid sequence of nucleotide 1112 to nucleotide 1171 of SEQ ID NO: 2.

13. The nucleic acid of claim 11, wherein the peptide comprises amino acid residues 321 to 346 of SEQ ID NO:1.

14. The nucleic acid of claim 13 wherein the peptide comprises amino acid residues 320 to 350 of SEQ ID NO:1.

15. The nucleic acid of claim 14 wherein the peptide comprises amino acid residues 312 to residue 361 of SEQ ID NO:1.

16. The nucleic acid of claim 11 wherein the peptide comprises a specific neutralization epitope for an anti-GDF8 antibody.

17. The nucleic acid of claim 16, wherein the antibody is selected from the group consisting of rat anti-GDF8 monoclonal antibody 788 and an IgG fraction of goat anti-GDF8 polyclonal antiserum.

18. A vector comprising the nucleic acid molecule of claim 16.

19. A vector comprising the nucleic acid molecule of claim 11.

20. A host cell comprising the vector of claim 19.

21. The host cell of claim 20 that is a eukaryotic cell.

22. A method of producing a GDF8 peptide comprising the steps of culturing the host cell of claim 20, and expressing the encoded peptide.

23. The method of claim 22, further comprising the step of recovering the GDF8 peptide.

24. A nucleic acid molecule that encodes a fusion protein, said nucleic acid molecule comprising (i) a nucleotide sequence that encodes a peptide consisting of 50 or fewer amino acid residues that comprises amino acid residues 327 to 346 of SEQ ID NO:1 comprising one or more amino acid substitutions; wherein there are no more than five amino acid substitutions between amino acid residues 327 to residue 346; and (ii) a heterologous nucleotide sequence; wherein the peptide specifically binds to rat monoclonal antibody 788.

25. A vector comprising the nucleic acid molecule of claim 24.

* * * * *

SEQUENCE LISTING

```
<160> NUMBER OF SEQ ID NOS: 36

<210> SEQ ID NO 1
<211> LENGTH: 375
<212> TYPE: PRT
<213> ORGANISM: Human
<220> FEATURE:
<221> NAME/KEY: Peptide
<222> LOCATION: (267)..(286)
<223> OTHER INFORMATION: DJ1
<220> FEATURE:
<221> NAME/KEY: Peptide
<222> LOCATION: (282)..(301)
<223> OTHER INFORMATION: DJ2
<220> FEATURE:
<221> NAME/KEY: Peptide
<222> LOCATION: (297)..(316)
<223> OTHER INFORMATION: DJ3
<220> FEATURE:
<221> NAME/KEY: Peptide
<222> LOCATION: (312)..(331)
<223> OTHER INFORMATION: DJ4
<220> FEATURE:
<221> NAME/KEY: Peptide
<222> LOCATION: (327)..(346)
<223> OTHER INFORMATION: DJ5
<220> FEATURE:
<221> NAME/KEY: Peptide
<222> LOCATION: (342)..(361)
<223> OTHER INFORMATION: DJ6
<220> FEATURE:
<221> NAME/KEY: Peptide
<222> LOCATION: (357)..(375)
<223> OTHER INFORMATION: DJ7

<400> SEQUENCE: 1

Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45
```

```
Lys Ser Ser Arg Ile Glu Ala Ile Lys Ile Gln Ile Leu Ser Lys Leu
     50                  55                  60

Arg Leu Glu Thr Ala Pro Asn Ile Ser Lys Asp Val Ile Arg Gln Leu
 65                  70                  75                  80

Leu Pro Lys Ala Pro Pro Leu Arg Glu Leu Ile Asp Gln Tyr Asp Val
                 85                  90                  95

Gln Arg Asp Asp Ser Ser Asp Gly Ser Leu Glu Asp Asp Tyr His
             100                 105                 110

Ala Thr Thr Glu Thr Ile Ile Thr Met Pro Thr Glu Ser Asp Phe Leu
             115                 120                 125

Met Gln Val Asp Gly Lys Pro Lys Cys Cys Phe Phe Lys Phe Ser Ser
     130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175

Ile Lys Pro Met Lys Asp Gly Thr Arg Tyr Thr Gly Ile Arg Ser Leu
                180                 185                 190

Lys Leu Asp Met Asn Pro Gly Thr Gly Ile Trp Gln Ser Ile Asp Val
     195                 200                 205

Lys Thr Val Leu Gln Asn Trp Leu Lys Gln Pro Glu Ser Asn Leu Gly
210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
                260                 265                 270

Asp Glu His Ser Thr Glu Ser Arg Cys Cys Arg Tyr Pro Leu Thr Val
             275                 280                 285

Asp Phe Glu Ala Phe Gly Trp Asp Trp Ile Ile Ala Pro Lys Arg Tyr
     290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
             340                 345                 350

Phe Asn Gly Lys Glu Gln Ile Ile Tyr Gly Lys Ile Pro Ala Met Val
     355                 360                 365

Val Asp Arg Cys Gly Cys Ser
370                 375

<210> SEQ ID NO 2
<211> LENGTH: 2823
<212> TYPE: DNA
<213> ORGANISM: Human
<220> FEATURE:
<221> NAME/KEY: misc_feature
<222> LOCATION: (134)..(1261)
<223> OTHER INFORMATION: Encodes Precursor GDF8
<220> FEATURE:
<221> NAME/KEY: Peptide
<222> LOCATION: (1112)..(1171)
<223> OTHER INFORMATION: Encodes DJ5

<400> SEQUENCE: 2
```

```
agattcactg gtgtggcaag ttgtctctca gactgtacat gcattaaaat tttgcttggc    60
attactcaaa agcaaagaa aagtaaaagg aagaaacaag aacaagaaaa aagattatat   120
tgattttaaa atcatgcaaa aactgcaact ctgtgtttat atttacctgt ttatgctgat   180
tgttgctggt ccagtggatc taaatgagaa cagtgagcaa aaagaaaatg tggaaaaaga   240
ggggctgtgt aatgcatgta cttggagaca aaacactaaa tcttcaagaa tagaagccat   300
taagatacaa atcctcagta aacttcgtct ggaaacagct cctaacatca gcaaagatgt   360
tataagacaa cttttaccca aagctcctcc actccgggaa ctgattgatc agtatgatgt   420
ccagagggat gacagcagcg atggctcttt ggaagatgac gattatcacg ctacaacgga   480
aacaatcatt accatgccta cagagtctga ttttctaatg caagtggatg aaaacccaa    540
atgttgcttc tttaaattta gctctaaaat acaatacaat aaagtagtaa aggcccaact   600
atggatatat ttgagacccg tcgagactcc tacaacagtg tttgtgcaaa tcctgagact   660
catcaaacct atgaaagacg gtacaaggta tactggaatc cgatctctga aacttgacat   720
gaacccaggc actggtattt ggcagagcat tgatgtgaag acagtgttgc aaaattggct   780
caaacaacct gaatccaact taggcattga aataaaagct ttagatgaga atggtcatga   840
tcttgctgta accttcccag gaccaggaga agatgggctg aatccgtttt tagaggtcaa   900
ggtaacagac acaccaaaaa gatccagaag ggattttggt cttgactgtg atgagcactc   960
aacagaatca cgatgctgtc gttaccctct aactgtggat tttgaagctt tggatgggga  1020
ttggattatc gctcctaaaa gatataaggc caattactgc tctggagagt gtgaatttgt  1080
attttacaa aaatatcctc atactcatct ggtacaccaa gcaaacccca gaggttcagc   1140
aggcccttgc tgtactccca caaagatgtc tccaattaat atgctatatt ttaatggcaa  1200
agaacaaata atatatggga aaattccagc gatggtagta daccgctgtg ggtgctcatg  1260
agatttatat taagcgttca taacttccta aaacatggaa ggttttcccc tcaacaattt  1320
tgaagctgtg aaattaagta ccacaggcta taggcctaga gtatgctaca gtcacttaag  1380
cataagctac agtatgtaaa ctaaaagggg gaatatatgc aatggttggc atttaaccat  1440
ccaaacaaat catacaagaa agttttatga tttccagagt ttttgagcta gaaggagatc  1500
aaattacatt tatgttccta tatattacaa catcggcgag gaaatgaaag cgattctcct  1560
tgagttctga tgaattaaag gagtatgctt taaagtctat ttctttaaag ttttgtttaa  1620
tatttacaga aaaatccaca tacagtattg gtaaaatgca ggattgttat ataccatcat  1680
tcgaatcatc cttaaacact tgaatttata ttgtatggta gtatacttgg taagataaaa  1740
ttccacaaaa atagggatgg tgcagcatat gcaatttcca ttcctattat aattgacaca  1800
gtacattaac aatccatgcc aacggtgcta atacgatagg ctgaatgtct gaggctacca  1860
ggtttatcac ataaaaaaca ttcagtaaaa tagtaagttt ctcttttctt caggggcatt  1920
ttcctacacc tccaaatgag gaatggattt tctttaatgt aagaagaatc attttctag    1980
aggttggctt tcaattctgt agcatacttg gagaaactgc attatcttaa aaggcagtca  2040
aatggtgttt gttttatca aaatgtcaaa ataacatact tggagaagta tgtaattttg   2100
tcttggaaa attcaacac tgcctttgca acactgcagt ttttatggta aaataataga   2160
aatgatcgac tctatcaata ttgtataaaa agactgaaac aatgcattta tataatatgt  2220
atacaatatt gttttgtaaa taagtgtctc cttttttatt tactttggta tattttaca   2280
ctaaggacat ttcaaattaa gtactaaggc acaaagacat gtcatgcatc acagaaaagc  2340
aactacttat atttcagagc aaattagcag attaaatagt ggtcttaaaa ctccatatgt  2400
```

-continued

```
taatgattag atggttatat tacaatcatt ttatattttt ttacatgatt aacattcact    2460
tatggattca tgatggctgt ataaagtgaa tttgaaattt caatggttta ctgtcattgt    2520
gtttaaatct caacgttcca ttattttaat acttgcaaaa acattactaa gtataccaaa    2580
ataattgact ctattatctg aaatgaagaa taaactgatg ctatctcaac aataactgtt    2640
acttttattt tataatttga taatgaatat atttctgcat ttatttactt ctgttttgta    2700
aattgggatt ttgttaatca aatttattgt actatgacta aatgaaatta tttcttacat    2760
ctaatttgta gaaacagtat aagttatatt aaagtgtttt cacattttttt tgaaagacaa    2820 aaa                                                                   2823

<210> SEQ ID NO 3
<211> LENGTH: 1164
<212> TYPE: DNA
<213> ORGANISM: Artificial Sequence
<220> FEATURE:
<223> OTHER INFORMATION: GDF8 prohormone FLAG tag fusion protein
<220> FEATURE:
<221> NAME/KEY: sig_peptide
<222> LOCATION: (10)..(75)
<220> FEATURE:
<221> NAME/KEY: misc_feature
<222> LOCATION: (76)..(1131)
<223> OTHER INFORMATION: Encodes Precursor GDF8
<220> FEATURE:
<221> NAME/KEY: Peptide
<222> LOCATION: (985)..(1044)
<223> OTHER INFORMATION: Encodes DJ5 Peptide
<220> FEATURE:
<221> NAME/KEY: misc_feature
<222> LOCATION: (1132)..(1161)
<223> OTHER INFORMATION: Encodes C-terminal FLAG tag

<400> SEQUENCE: 3
atggatctac agaagttgca gttgtgtgtc tacatctatt tgttcatgtt gatcgtcgcc      60
ggacctgttg acttgaacga aaattctgaa cagaaggaga acgttgagaa ggaaggtttg     120
tgcaacgctt gtacatggcg tcaaaataca aagtcctctc gtattgaagc tatcaagatt     180
caaattttgt ctaagttgag attggaaact gccccaaata tttctaagga cgtcattcgt     240
caattgttgc caaaggcccc acctttgaga gaattgatcg accaatacga tgttcaaaga     300
gacgattctt ctgacggttc ccttgaagac gatgactacc atgccactac tgaaactatt     360
atcactatgc caactgaatc cgactttttg atgcaggttg atggtaagcc aaagtgctgt     420
tttttcaagt tctcttccaa gattcaatac aacaaggttg ttaaagctca attgtggatt     480
taccttcgtc cagttgaaac accaactact gtgtttgttc agattttgcg tttgattaag     540
ccaatgaagg atggaactag atacacaggt attagatcct tgaagttgga tatgaatcct     600
ggtacaggaa tctggcaatc tatcgacgtt aaaactgttc ttcaaaactg gttgaagcaa     660
ccagagtcta atttgggtat cgagattaag gccttggacg aaaacggaca tgacttggcc     720 gttactttc ctggtcctgg tgaagacggt ttgaacccat ttctggaagt taaggttact     780
gatactccta agcgttccag gagagacttc ggattggatt gtgatgaaca ttctactgag     840
tctagatgtt gtagatatcc attgaccgtt gatttcgagg ccttcggttg ggattggatc     900
attgccccaa agagatacaa agctaactat tgttccggtg aatgtgagtt cgttttcttg     960
cagaagtacc cacataccca tttggttcat caggctaatc aagaggatc tgctggtcca    1020 tgttgtaccc caactaaaat gtcccctatc aacatgttgt acttcaacgg taaggagcag    1080
attatttacg gtaagatccc tgctatggtt gttgatagat gtggttgttc tctcgaggat    1140
```
tacaaggatg acgacgataa gtag                                          1164

<210> SEQ ID NO 4
<211> LENGTH: 20
<212> TYPE: PRT
<213> ORGANISM: Human
<220> FEATURE:
<221> NAME/KEY: misc_feature
<223> OTHER INFORMATION: DJ1

<400> SEQUENCE: 4

Asp Phe Gly Leu Asp Cys Asp Glu His Ser Thr Glu Ser Arg Cys Cys
1               5                   10                  15

Arg Tyr Pro Leu
            20

<210> SEQ ID NO 5
<211> LENGTH: 20
<212> TYPE: PRT
<213> ORGANISM: Human
<220> FEATURE:
<221> NAME/KEY: misc_feature
<223> OTHER INFORMATION: DJ2

<400> SEQUENCE: 5

Cys Arg Tyr Pro Leu Thr Val Asp Phe Glu Ala Phe Gly Trp Asp Trp
1               5                   10                  15

Ile Ile Ala Pro
            20

<210> SEQ ID NO 6
<211> LENGTH: 20
<212> TYPE: PRT
<213> ORGANISM: Human
<220> FEATURE:
<221> NAME/KEY: misc_feature
<223> OTHER INFORMATION: DJ3

<400> SEQUENCE: 6

Trp Ile Ile Ala Pro Lys Arg Tyr Lys Ala Asn Tyr Cys Ser Gly Glu
1               5                   10                  15

Cys Glu Phe Val
            20

<210> SEQ ID NO 7
<211> LENGTH: 20
<212> TYPE: PRT
<213> ORGANISM: Human
<220> FEATURE:
<221> NAME/KEY: misc_feature
<223> OTHER INFORMATION: DJ4

<400> SEQUENCE: 7

Glu Cys Glu Phe Val Phe Leu Gln Lys Tyr Pro His Thr His Leu Val
1               5                   10                  15

His Gln Ala Asn
            20

<210> SEQ ID NO 8
<211> LENGTH: 20
<212> TYPE: PRT
<213> ORGANISM: Human
<220> FEATURE:
<221> NAME/KEY: misc_feature
<223> OTHER INFORMATION: DJ5

```
<400> SEQUENCE: 8

Val His Gln Ala Asn Pro Arg Gly Ser Ala Gly Pro Cys Cys Thr Pro
1               5                   10                  15

Thr Lys Met Ser
            20

<210> SEQ ID NO 9
<211> LENGTH: 20
<212> TYPE: PRT
<213> ORGANISM: Human
<220> FEATURE:
<221> NAME/KEY: misc_feature
<223> OTHER INFORMATION: DJ6

<400> SEQUENCE: 9

Pro Thr Lys Met Ser Pro Ile Asn Met Leu Tyr Phe Asn Gly Lys Glu
1               5                   10                  15

Gln Ile Ile Tyr
            20

<210> SEQ ID NO 10
<211> LENGTH: 20
<212> TYPE: PRT
<213> ORGANISM: Human
<220> FEATURE:
<221> NAME/KEY: misc_feature
<223> OTHER INFORMATION: DJ7

<400> SEQUENCE: 10

Val His Gln Ala Asn Pro Arg Gly Ser Ala Gly Pro Cys Cys Thr Pro
1               5                   10                  15

Thr Lys Met Ser
            20

<210> SEQ ID NO 11
<211> LENGTH: 20
<212> TYPE: PRT
<213> ORGANISM: Anas platyrhynchos

<400> SEQUENCE: 11

Val His Gln Ala Asn Pro Arg Gly Ser Ala Gly Pro Cys Cys Thr Pro
1               5                   10                  15

Thr Lys Met Ser
            20

<210> SEQ ID NO 12
<211> LENGTH: 20
<212> TYPE: PRT
<213> ORGANISM: Anser anser

<400> SEQUENCE: 12

Val His Gln Ala Asn Pro Arg Gly Ser Ala Gly Pro Cys Cys Thr Pro
1               5                   10                  15

Thr Lys Met Ser
            20

<210> SEQ ID NO 13
<211> LENGTH: 20
<212> TYPE: PRT
<213> ORGANISM: Anser anser

<400> SEQUENCE: 13
```

```
Val Leu Gln Ala Asn Pro Arg Gly Ser Ala Gly Pro Cys Cys Thr Pro
1               5                   10                  15

Thr Lys Met Ser
            20

<210> SEQ ID NO 14
<211> LENGTH: 20
<212> TYPE: PRT
<213> ORGANISM: Bos taurus

<400> SEQUENCE: 14

Val His Gln Ala Asn Pro Arg Gly Ser Ala Gly Pro Cys Cys Thr Pro
1               5                   10                  15

Thr Lys Met Ser
            20

<210> SEQ ID NO 15
<211> LENGTH: 20
<212> TYPE: PRT
<213> ORGANISM: Canis familiaris

<400> SEQUENCE: 15

Val His Gln Ala Asn Pro Arg Gly Ser Ala Gly Pro Cys Cys Thr Pro
1               5                   10                  15

Thr Lys Met Ser
            20

<210> SEQ ID NO 16
<211> LENGTH: 20
<212> TYPE: PRT
<213> ORGANISM: Capra hircus

<400> SEQUENCE: 16

Val His Gln Ala Asn Pro Lys Gly Ser Ala Gly Pro Cys Cys Thr Pro
1               5                   10                  15

Thr Lys Met Ser
            20

<210> SEQ ID NO 17
<211> LENGTH: 20
<212> TYPE: PRT
<213> ORGANISM: Columba livia

<400> SEQUENCE: 17

Val His Gln Ala Asn Pro Arg Gly Ser Ala Gly Pro Cys Cys Thr Pro
1               5                   10                  15

Thr Lys Met Ser
            20

<210> SEQ ID NO 18
<211> LENGTH: 20
<212> TYPE: PRT
<213> ORGANISM: Coturnix chinensis

<400> SEQUENCE: 18

Val His Gln Ala Asn Pro Arg Gly Ser Ala Gly Pro Cys Cys Thr Pro
1               5                   10                  15

Thr Lys Met Ser
            20

<210> SEQ ID NO 19
<211> LENGTH: 20
```

```
<212> TYPE: PRT
<213> ORGANISM: Danio rerio

<400> SEQUENCE: 19

Val Asn Lys Ala Ser Pro Arg Gly Thr Ala Gly Pro Cys Cys Thr Pro
1               5                   10                  15

Thr Lys Met Ser
            20

<210> SEQ ID NO 20
<211> LENGTH: 20
<212> TYPE: PRT
<213> ORGANISM: Equus caballus

<400> SEQUENCE: 20

Val His Gln Ala Asn Pro Arg Gly Ser Ala Gly Pro Cys Cys Thr Pro
1               5                   10                  15

Thr Lys Met Ser
            20

<210> SEQ ID NO 21
<211> LENGTH: 20
<212> TYPE: PRT
<213> ORGANISM: Gallus gallus

<400> SEQUENCE: 21

Val His Gln Ala Asn Pro Arg Gly Pro Ala Gly Pro Cys Cys Thr Pro
1               5                   10                  15

Thr Lys Met Ser
            20

<210> SEQ ID NO 22
<211> LENGTH: 20
<212> TYPE: PRT
<213> ORGANISM: Gallus gallus

<400> SEQUENCE: 22

Val His Gln Ala Asn Pro Arg Gly Ser Ala Gly Pro Cys Cys Thr Pro
1               5                   10                  15

Thr Lys Met Ser
            20

<210> SEQ ID NO 23
<211> LENGTH: 20
<212> TYPE: PRT
<213> ORGANISM: I. punctatus

<400> SEQUENCE: 23

Val Asn Lys Ala Ser Pro Arg Gly Thr Ala Gly Pro Cys Cys Thr Pro
1               5                   10                  15

Thr Lys Met Ser
            20

<210> SEQ ID NO 24
<211> LENGTH: 20
<212> TYPE: PRT
<213> ORGANISM: Lepus capensis

<400> SEQUENCE: 24

Val His Gln Ala Asn Pro Arg Gly Ser Ala Gly Pro Cys Cys Thr Pro
1               5                   10                  15

Thr Lys Met Ser
```

```
                 20

<210> SEQ ID NO 25
<211> LENGTH: 20
<212> TYPE: PRT
<213> ORGANISM: Macaca fascicularis

<400> SEQUENCE: 25

Val His Gln Ala Asn Pro Arg Gly Ser Ala Gly Pro Cys Cys Thr Pro
1               5                   10                  15

Thr Lys Met Ser
            20

<210> SEQ ID NO 26
<211> LENGTH: 20
<212> TYPE: PRT
<213> ORGANISM: Meleagris gallopavo

<400> SEQUENCE: 26

Val His Gln Ala Asn Pro Arg Gly Ser Ala Gly Pro Cys Cys Thr Pro
1               5                   10                  15

Thr Lys Met Ser
            20

<210> SEQ ID NO 27
<211> LENGTH: 20
<212> TYPE: PRT
<213> ORGANISM: Morone chrysops

<400> SEQUENCE: 27

Val Asn Lys Ala Asn Pro Arg Gly Thr Ala Gly Pro Cys Cys Thr Pro
1               5                   10                  15

Thr Lys Met Ser
            20

<210> SEQ ID NO 28
<211> LENGTH: 20
<212> TYPE: PRT
<213> ORGANISM: Mus musculus

<400> SEQUENCE: 28

Val His Gln Ala Asn Pro Arg Gly Ser Ala Gly Pro Cys Cys Thr Pro
1               5                   10                  15

Thr Lys Met Ser
            20

<210> SEQ ID NO 29
<211> LENGTH: 20
<212> TYPE: PRT
<213> ORGANISM: O. mykiss

<400> SEQUENCE: 29

Val Asn Lys Ala Asn Pro Arg Gly Thr Ala Gly Pro Cys Cys Thr Pro
1               5                   10                  15

Thr Lys Met Ser
            20

<210> SEQ ID NO 30
<211> LENGTH: 20
<212> TYPE: PRT
<213> ORGANISM: Ovis aries

<400> SEQUENCE: 30
```

-continued

Val His Gln Ala Asn Pro Lys Gly Ser Ala Gly Pro Cys Cys Thr Pro
1               5                   10                  15

Thr Lys Met Ser
            20

<210> SEQ ID NO 31
<211> LENGTH: 20
<212> TYPE: PRT
<213> ORGANISM: Papio hamadryas

<400> SEQUENCE: 31

Val His Gln Ala Asn Pro Arg Gly Ser Ala Gly Pro Cys Cys Thr Pro
1               5                   10                  15

Thr Lys Met Ser
            20

<210> SEQ ID NO 32
<211> LENGTH: 20
<212> TYPE: PRT
<213> ORGANISM: Rattus norvegicus

<400> SEQUENCE: 32

Val His Gln Ala Asn Pro Arg Gly Ser Ala Gly Pro Cys Cys Thr Pro
1               5                   10                  15

Thr Lys Met Ser
            20

<210> SEQ ID NO 33
<211> LENGTH: 20
<212> TYPE: PRT
<213> ORGANISM: Salmo salar

<400> SEQUENCE: 33

Val Asn Lys Ala Asn Pro Arg Gly Thr Ala Gly Pro Cys Cys Thr Pro
1               5                   10                  15

Thr Lys Met Ser
            20

<210> SEQ ID NO 34
<211> LENGTH: 20
<212> TYPE: PRT
<213> ORGANISM: Sparus aurata

<400> SEQUENCE: 34

Val Asn Lys Ala Asn Pro Arg Gly Thr Ala Gly Pro Cys Cys Thr Pro
1               5                   10                  15

Thr Lys Met Ser
            20

<210> SEQ ID NO 35
<211> LENGTH: 20
<212> TYPE: PRT
<213> ORGANISM: Sus scrofa

<400> SEQUENCE: 35

Val His Gln Ala Asn Pro Arg Gly Ser Ala Gly Pro Cys Cys Thr Pro
1               5                   10                  15

Thr Lys Met Ser
            20

<210> SEQ ID NO 36

```
-continued

<211> LENGTH: 20
<212> TYPE: PRT
<213> ORGANISM: Sus scrofa

<400> SEQUENCE: 36

Val Leu Gln Ala Asn Pro Arg Gly Ser Ala Gly Pro Cys Cys Thr Pro
1               5                   10                  15

Thr Lys Met Ser
            20
```